(12) United States Patent
Hurst et al.

(10) Patent No.: US 11,707,613 B2
(45) Date of Patent: Jul. 25, 2023

(54) SURGICAL PORT FEATURES WITH ELECTRICALLY CONDUCTIVE PORTIONS, RELATED DEVICES, AND RELATED METHODS

(71) Applicant: INTUITIVE SURGICAL OPERATIONS, INC., Sunnyvale, CA (US)

(72) Inventors: Michael Hurst, San Francisco, CA (US); Sam Crews, Palomar Park, CA (US); Bryan E. Blair, Santa Clara, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 565 days.

(21) Appl. No.: 16/825,421

(22) Filed: Mar. 20, 2020

(65) Prior Publication Data

US 2020/0230392 A1    Jul. 23, 2020

Related U.S. Application Data

(63) Continuation of application No. 15/877,767, filed on Jan. 23, 2018, now Pat. No. 10,617,858.
(Continued)

(51) Int. Cl.
*A61M 39/02* (2006.01)
*A61B 1/00* (2006.01)
(Continued)

(52) U.S. Cl.
CPC ..... *A61M 39/0247* (2013.01); *A61B 1/00154* (2013.01); *A61B 1/313* (2013.01);
(Continued)

(58) Field of Classification Search
CPC ...... A61M 39/0247; A61M 2039/0264; A61M 2039/0267; A61M 2039/0279;
(Continued)

(56) References Cited

U.S. PATENT DOCUMENTS

| 5,507,758 A | 4/1996 | Thomason et al. |
| 6,508,759 B1 | 1/2003 | Taylor et al. |

(Continued)

FOREIGN PATENT DOCUMENTS

| WO | WO-03091608 A2 | 11/2003 |
| WO | WO-2008103151 A2 | 8/2008 |
| WO | WO-2009080399 A2 | 7/2009 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Eduardo C Robert
*Assistant Examiner* — David C Comstock
(74) *Attorney, Agent, or Firm* — Jones Robb, PLLC

(57) ABSTRACT

A surgical port includes a first end, a second end opposite the first end, and a longitudinal axis extending through the first end and the second end. An outer sidewall extends between the first end and the second end. First and second channels extend through the port from the first end to the second end. A first electrically conductive portion extends from the first channel to the outer sidewall, and a second electrically conductive portion extends from the second channel to the outer sidewall. The first electrically conductive portion provides a first electrically conductive path between the first channel and the outer sidewall and the second electrically conductive portion provides a second electrically conductive path the second channel and the outer sidewall. The second (Continued)

electrically conductive path is separate from the first electrically conductive path. Devices and methods relate to surgical ports.

19 Claims, 8 Drawing Sheets

Related U.S. Application Data

(60) Provisional application No. 62/449,822, filed on Jan. 24, 2017.

(51) Int. Cl.
| | |
|---|---|
| *A61B 17/34* | (2006.01) |
| *A61B 18/14* | (2006.01) |
| *A61B 1/313* | (2006.01) |
| *A61B 34/30* | (2016.01) |
| *A61B 34/35* | (2016.01) |
| *A61B 17/02* | (2006.01) |
| *A61B 17/00* | (2006.01) |
| *A61B 18/00* | (2006.01) |

(52) U.S. Cl.
CPC ...... *A61B 17/3423* (2013.01); *A61B 18/1482* (2013.01); *A61B 17/0218* (2013.01); *A61B 34/30* (2016.02); *A61B 34/35* (2016.02); *A61B 2017/00526* (2013.01); *A61B 2017/3445* (2013.01); *A61B 2017/3449* (2013.01); *A61B 2017/3466* (2013.01); *A61B 2018/00077* (2013.01); *A61B 2034/302* (2016.02); *A61M 2039/0264* (2013.01); *A61M 2039/0267* (2013.01); *A61M 2039/0279* (2013.01); *A61M 2039/0294* (2013.01); *A61M 2207/00* (2013.01)

(58) Field of Classification Search
CPC ...... A61M 2039/0294; A61M 2207/00; A61B 1/00154; A61B 1/313; A61B 18/1482; A61B 34/30; A61B 34/35; A61B 2034/302; A61B 17/3423; A61B 17/0218; A61B 2017/00526; A61B 2017/3445; A61B 2017/3449; A61B 2017/3466; A61B 2018/00077
USPC ................. 600/204, 205, 206, 208, 210
See application file for complete search history.

(56) References Cited

U.S. PATENT DOCUMENTS

| | | | |
|---|---|---|---|
| 6,551,270 | B1 | 4/2003 | Bimbo et al. |
| 7,650,887 | B2 | 1/2010 | Nguyen et al. |
| 8,545,515 | B2 | 10/2013 | Prisco et al. |
| 8,852,208 | B2 | 10/2014 | Gomez et al. |
| 9,877,744 | B2 | 1/2018 | Cooper et al. |
| 10,070,887 | B2 | 9/2018 | Lambrecht et al. |
| 10,617,858 | B2 * | 4/2020 | Hurst ................ A61B 17/3423 |
| 2006/0247500 | A1 | 11/2006 | Voegele et al. |
| 2009/0012477 | A1 | 1/2009 | Norton et al. |
| 2009/0093752 | A1 | 4/2009 | Richard et al. |
| 2009/0131751 | A1 | 5/2009 | Spivey et al. |
| 2011/0282358 | A1 * | 11/2011 | Gomez ................ H04N 5/2253 606/130 |
| 2012/0078245 | A1 * | 3/2012 | Morrissette ........... A61B 18/14 606/34 |
| 2013/0096555 | A1 | 4/2013 | Krom et al. |
| 2013/0325031 | A1 | 12/2013 | Schena et al. |
| 2013/0325033 | A1 | 12/2013 | Schena et al. |
| 2017/0231477 | A1 | 8/2017 | Del et al. |
| 2018/0132890 | A1 * | 5/2018 | Morrissette ........... A61B 18/14 |
| 2018/0221639 | A1 | 8/2018 | Hurst et al. |

* cited by examiner

SURGICAL PORT FEATURES WITH ELECTRICALLY CONDUCTIVE PORTIONS, RELATED DEVICES, AND RELATED METHODS

RELATED APPLICATIONS

This application is a continuation application of U.S. application Ser. No. 15/877,767, filed Jan. 23, 2018, which claims priority to Provisional U.S. Patent Application No. 62/449,822, filed on Jan. 24, 2017, which is incorporated by reference herein in its entirety.

TECHNICAL FIELD

Aspects of the present disclosure relate to surgical port features including electrically conductive portions.

INTRODUCTION

Various surgical instruments or tools can be positioned to extend through cannulas passing through a surgical port positioned in an incision of a patient's body wall. Such instruments or tools may be configured to apply electrical energy to an operating site to carry out a surgical procedure. For example, a surgical instrument may be configured to seal, bond, ablate, fulgurate, or perform other treatments of tissue through the application of an electrical current. Additionally, a surgical instrument can be an optical instrument, such as an endoscope, positioned to extend through a cannula inserted through the surgical port. Such surgical instruments and tools include, without limitation, minimally invasive surgical instruments that are manually operated or teleoperated using computer-assisted technology. One example of a teleoperated, computer-assisted surgical system (e.g., a robotic system that provides telepresence) with which embodiments of the present disclosure may be used, are the da Vinci® Surgical Systems manufactured by Intuitive Surgical, Inc. of Sunnyvale, Calif.

In some situations, a capacitive coupling is induced between surgical instruments in proximity to each other by current applied to the one or more surgical instruments by an electro-surgical generator (e.g., electro-surgical unit (ESU)). In particular, capacitive coupling between an optical instrument, e.g., the endoscope, and other surgical instruments has potential to generate a leakage current that misdirects a portion of the current generated by the ESU, e.g., along a conductive cannula through which another surgical instrument extends. Such capacitive coupling may occur between multiple instruments extending through a single port, or between multiple instruments extending through separate, respective ports. However, because multiple instruments passing through a single port are typically positioned close to one another, and because capacitive coupling generally increases with physical proximity of the instruments, the leakage current as described above may pose a greater problem when multiple instruments extend through a single port.

Some surgical ports are manufactured from polymer materials, such as, for example, silicone rubber in order to provide flexibility and durability, which may be desired to permit temporary and elastic deformation of the port during insertion into an incision in the patient's body wall. Such polymers are typically good electrical insulators. However, to mitigate capacitive coupling between instruments, it is desirable to dissipate energy from the respective cannulas through which the instruments extend and through the port to ground, (e.g., to the patient's body held at a ground potential). Thus, a need exists to provide a port with the desired flexibility and durability while also permitting dissipation of electrical energy from the surgical instruments to reduce or eliminate capacitive coupling between the instruments.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a surgical port includes a first end, a second end opposite the first end, and a longitudinal axis extending through the first end and the second end. An outer sidewall extends between the first end and the second end. First and second channels extend through the port from the first end to the second end. A first electrically conductive portion extends from the first channel to the outer sidewall, and a second electrically conductive portion extends from the second channel to the outer sidewall. The first electrically conductive portion provides a first electrically conductive path between the first channel and the outer sidewall and the second electrically conductive portion provides a second electrically conductive path between the second channel and the outer sidewall. The second conductive path is separate from the first electrically conductive path.

In accordance with at least another exemplary embodiment, a method of making a surgical port includes forming an electrically insulating body with a first negative feature defining a channel extending from a first end to a second end of the body and with a second negative feature extending from an opening in an inner surface of the channel to an opening in an outer sidewall of the electrically insulating body, and forming an electrically conductive portion within the second negative feature and extending from the opening in the inner surface of the channel to the opening in the outer sidewall. Forming the electrically conductive portion of the surgical port feature within the second negative feature comprises molding the electrically conductive portion over the electrically insulating portion.

In accordance with yet another exemplary embodiment, a surgical port includes a body portion having a first end, a second end, and a surgical instrument channel defined between the first end and the second end. An electrically conductive composite material extends from the channel through the body portion. The electrically conductive composite material comprises a continuous phase of a polymer matrix and a discontinuous phase of electrically conductive particles.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation. In the drawings.

DETAILED DESCRIPTION

Figure 1:
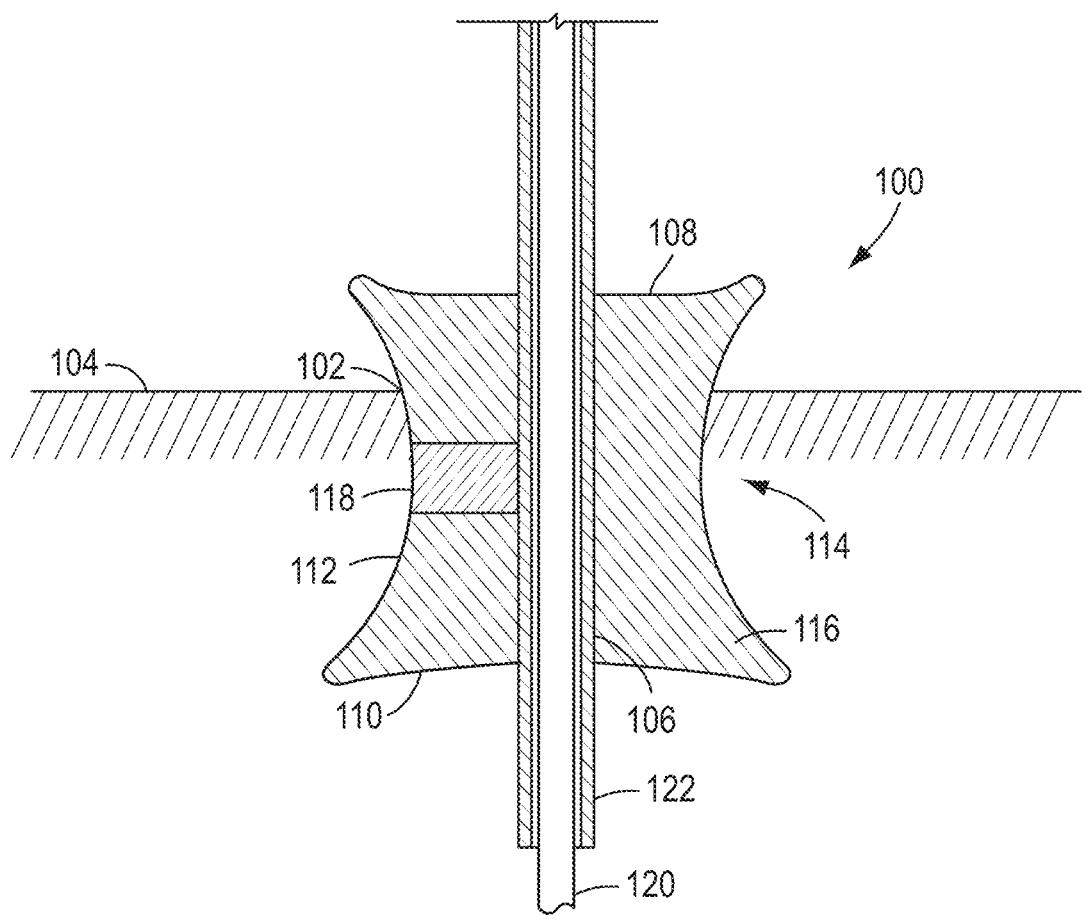
FIG. 1 is a cross-sectional elevation view of a surgical port and surgical instrument according to an exemplary embodiment of the disclosure.

The present disclosure contemplates various exemplary embodiments of surgical port features that include portions of material having a relatively low electrical conductivity and portions of material having relatively high electrical conductivity. In exemplary embodiments, the portions of material having relatively low electrical conductivity are made from a polymer, such as silicone rubber. The portions of material having relatively low electrical conductivity are a polymer, such as silicone rubber, with one or more electrically conductive materials in dispersed form in the material. Stated another way, the portions of material having relatively low electrical conductivity are a composite material including a continuous phase and a discontinuous phase. The continuous phase is polymer having a relatively low electrical conductivity, and the discontinuous phase is a material having a relatively high electrical conductivity. In exemplary embodiments, the discontinuous phase is comprised of particles having rod-like, spherical, or other shapes. In one exemplary embodiment, the discontinuous phase is carbon-fiber particles.

In exemplary embodiments, the surgical port feature is formed by an overmolding technique in which the high-conductivity material is molded to form the high-conductivity portion and the low-conductivity material is molded over the high-conductivity material. The surgical port feature optionally includes multiple portions of high-conductivity material separated by the low-conductivity material. In some exemplary embodiments, one or more of the surgical instruments, when inserted in the port, are electrically separated from one another by the low-conductivity material of the surgical port. For example, one or more instruments are individually electrically connected to the patient's body wall through respective, separate portions of high-conductivity material. Stated another way, in exemplary embodiments, the surgical port feature includes multiple different electrical pathways formed from internal surfaces surrounding passages in the port to external surfaces of the port configured to contact a patient's body wall when inserted in an incision.

Exemplary embodiments described herein may be used, for example, with teleoperated, computer-assisted surgical systems (sometimes referred to as robotic surgical systems) such as those described in, for example, U.S. Patent App. Pub. No. US 2013/0325033 A1 (published Dec. 5, 2013), entitled "Multi-Port Surgical Robotic System Architecture," U.S. Patent App. Pub. No. US 2013/0325031 A1 (published Dec. 5, 2013), entitled "Redundant Axis and Degree of Freedom for Hardware-Constrained Remote Center Robotic Manipulator," U.S. Pat. No. 8,852,208 (issued Oct. 7, 2014), entitled "Surgical System Instrument Mounting," and U.S. Pat. No. 8,545,515 (issued Oct. 1, 2013), entitled Curved Cannula Surgical System, each of which is hereby incorporated by reference in its entirety. Further, the exemplary embodiments described herein may be used, for example, with a da Vinci® Surgical System, such as the da Vinci Si® Surgical System or the da Vinci Xi® Surgical System, both with or without Single-Site® single orifice surgery technology, all commercialized by Intuitive Surgical, Inc. Although various exemplary embodiments described herein are discussed with regard to surgical instruments used with a patient side cart of a teleoperated surgical system, the present disclosure is not limited to use with surgical instruments for a teleoperated surgical system. For example, various exemplary embodiments of surgical ports described herein can optionally be used in conjunction with hand-held, manual surgical instruments, such as laparoscopic instruments.

Referring now to FIG. 1, an exemplary embodiment of a surgical port feature 100 according to the disclosure is shown. The surgical port feature 100 is positioned within an incision 102 in a body wall 104 of a patient. The surgical port feature 100 includes a channel 106 extending from a first surface (e.g., a first end) 108 to a second surface (e.g., a second end) 110 of the surgical port feature 100. An outer sidewall 112 of the surgical port feature 100 between the first surface 108 and the second surface 110 defines a narrowed waist portion 114 of the surgical port feature 100. The surgical port feature 100 includes a body portion 116 made from an electrically insulating material. An electrically conductive portion 118 comprising an electrically conductive material intersects the outer sidewall 112 and an interior surface of the channel 106, thereby forming an electrically conductive pathway between the channel 106 and the body wall 104.

A surgical instrument 120 is positioned within a cannula 122 extending through the channel 106. The cannula 122 is made from or includes a conductive material that forms an electrical pathway between the surgical instrument 120 and the electrically conductive portion 118 of the surgical port feature 100. The voltage potential of the surgical instrument 120 is thereby equalized with the electrical potential of the patient's body. In other words, the surgical instrument 120 is grounded to the patient's body through the cannula 122 and the electrically conductive portion 118 of the surgical port feature 100.

As shown in FIG. 1, the surgical instrument 120 is an endoscope. However, surgical instruments of any kind, such as other imaging instruments, surgical instruments with end effectors configured to manipulate or apply electrosurgical energy to tissue, end effectors configured to apply staples, clips, or other articles, or other end effectors, are considered to be within the scope of this disclosure.

Figure 2:
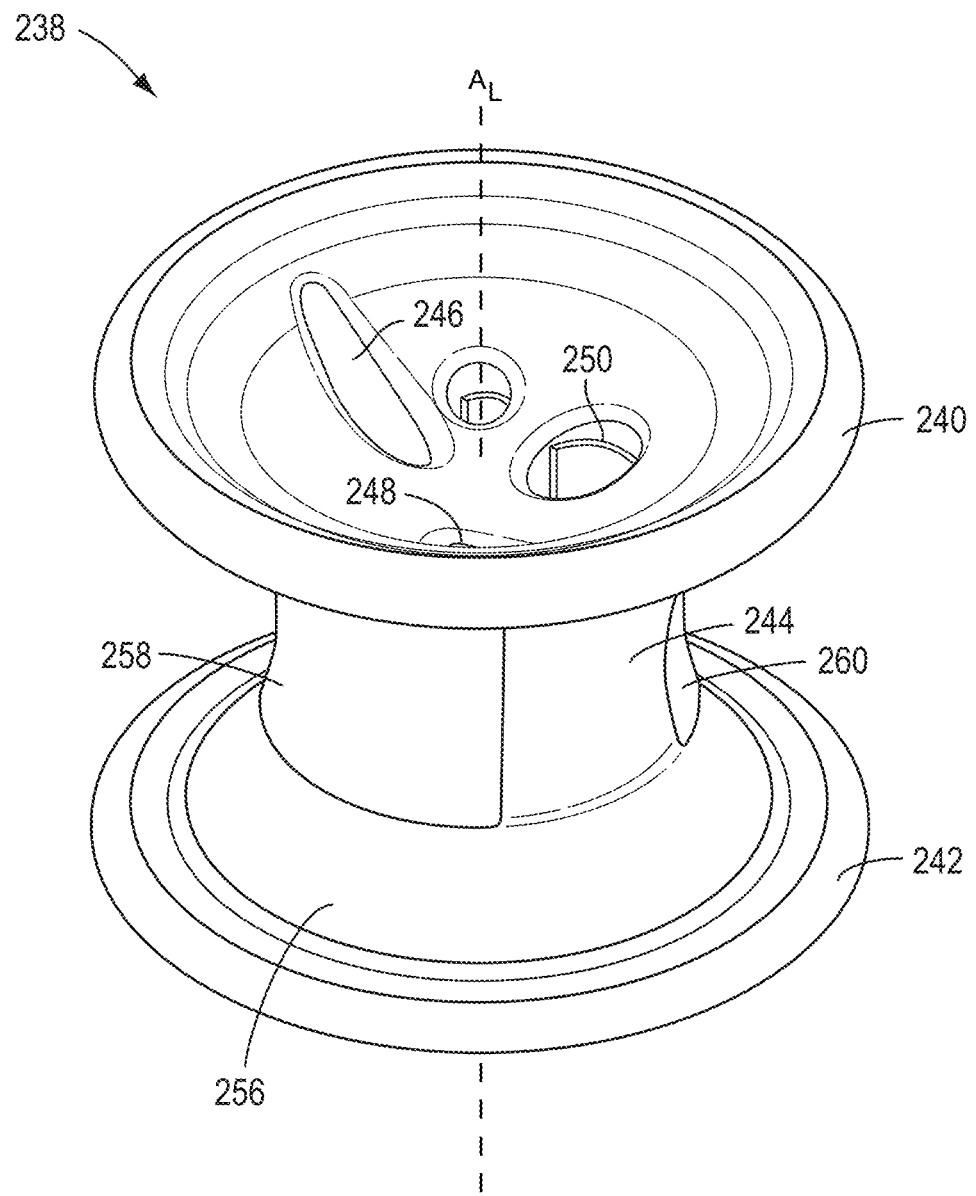
FIG. 2 is a perspective view of a surgical port according to another exemplary embodiment of the disclosure.
Figure 3:
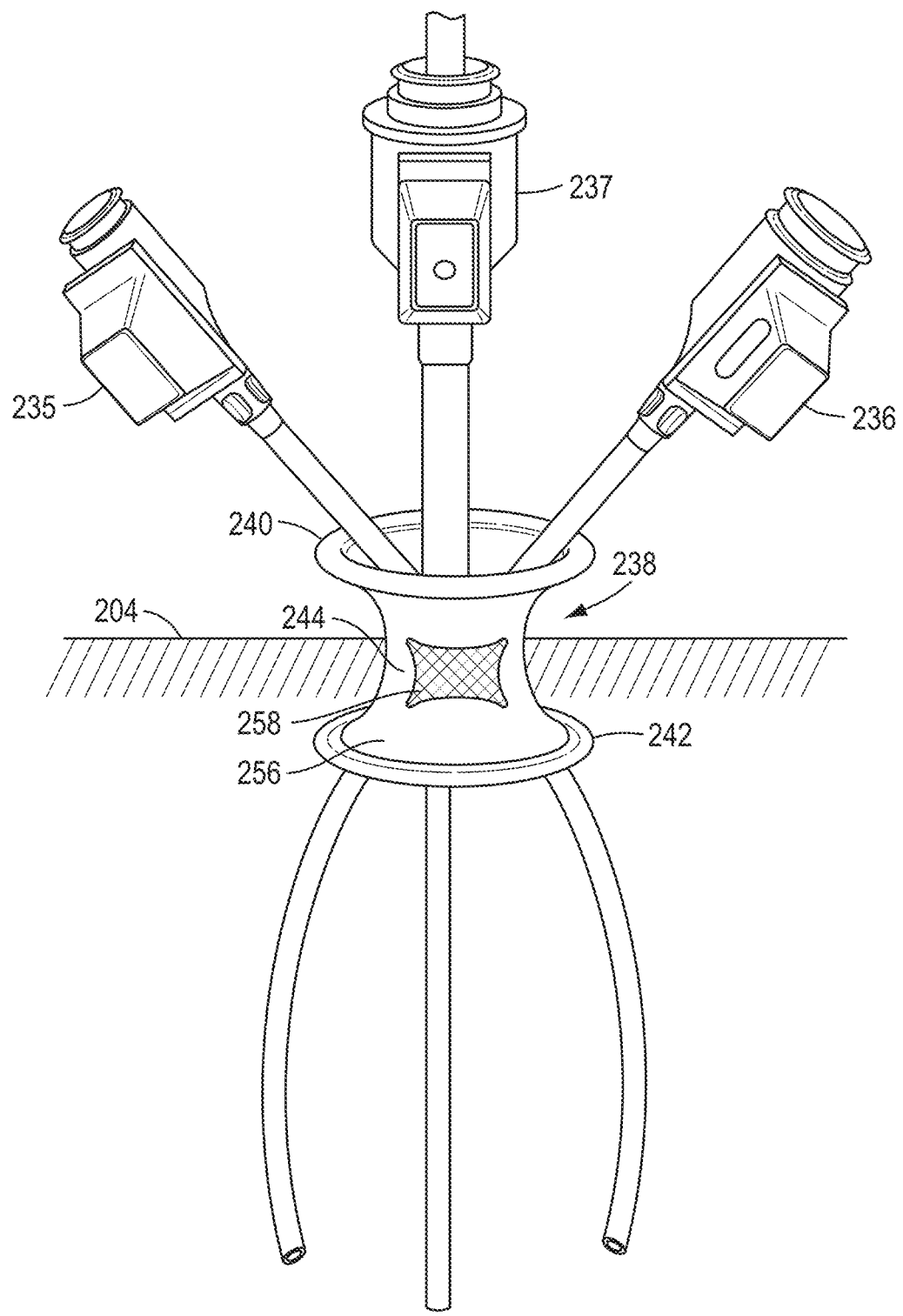
FIG. 3 is a perspective view of the surgical port of FIG. 2 with instrument cannulas according an exemplary embodiment.

Referring now to FIGS. 2 and 3, another exemplary embodiment of a surgical port feature 238 is shown. The surgical port feature 238 includes an upper flange 240 and a lower flange 242. The upper flange 240 defines a first surface (e.g., first end) 241 and the lower flange 242 defines a second surface (e.g., second end) 243 opposite the first surface 241. A narrowed waist portion 244 is located between the upper flange 240 and the lower flange 242 and defines an outer sidewall of the surgical port feature 238. A longitudinal axis $A_L$ extends through the first surface 241 and the second surface 243 of the surgical port feature 238. Channels 246, 248 (not fully visible in FIG. 2), and 250 configured to receive cannulas are formed through the surgical port feature 238 and extend between the upper flange 240 and lower flange 242. In use, the surgical port feature 238 is positioned in an incision in a patient's body wall 204 so that the upper flange 240 is positioned outside of the body wall 204, while the lower flange 242 is positioned within the body wall 204. At least a portion of the narrowed waist portion 244 contacts the patient's body wall 204 within the incision.

One or more surgical instruments (including, e.g., the endoscope 120 of FIG. 1) can each be positioned within a respective one of the cannulas 235, 236, and 237 extending through the channels 246, 248, and 250, respectively. In the exemplary embodiment of FIG. 3, the cannulas 235, 236, and 237 are made from conductive material or are otherwise configured to include a conductive path between an interior of the cannula and an exterior surface of the cannula, thus providing a conductive path between a surgical instrument positioned inside the cannula and the exterior of the cannula.

When surgical instruments configured to apply electrical current to the surgical site or instruments otherwise configured to operate using electrical current (e.g., imaging instruments such as the endoscope 120 of FIG. 1) are positioned within electrically conductive cannulas extending through the port and are subsequently energized, capacitive coupling between the instruments can result in misdirection of electrical energy by creating a leakage current through at least one of the conductive cannulas and the body of the patient. Thus, it is desirable to provide a surgical port feature 238 configured to enable predictable and consistent dissipation of an electrical current, such as a current generated by capacitive coupling between instruments inserted through the port, to the body ground through the material of the surgical port feature 238.

Accordingly, in the exemplary embodiment of FIGS. 2 and 3, the surgical port feature 238 includes a body portion 256 made from a first material exhibiting a relatively low electrical conductivity and one or more electrically conductive portions, such as electrically conductive portions 258, 260 made from a second material exhibiting a relatively higher electrical conductivity. The electrically conductive portions 258, 260 form a conductive path between an interior surface of a channel of the surgical port feature 238 (such as an interior surface of the one or more of channels 246, 248, and 250) and a portion of the surgical port feature 238 (e.g., a surface of the waist portion 244) configured to contact the patient's body when the surgical port feature 238 is positioned in the patient's body wall 204.

In exemplary embodiments, the first, electrically insulating material of the surgical port feature 238 exhibits mechanical characteristics such as a low hardness (e.g., high flexibility). As a non-limiting example, in some exemplary embodiments, the electrically insulating material of the surgical port feature 238 exhibits a hardness represented by a measurement of ranging from 0 to 50 on the Shore type A hardness scale. Factors for consideration in material choice include electrical characteristics, such as electrical resistivity, and mechanical characteristics, such as hardness, ultimate tensile strength, or other factors. As a specific, non-limiting example, the first, electrically insulating material of the surgical port feature 238 exhibits a durometer measurement of 10 on the Shore type A hardness scale. In various exemplary embodiments, the first, electrically insulating material of the surgical port feature 238 is silicone rubber.

The second, electrically conductive material from which the electrically conductive portions 258, 260 are formed is a material with mechanical characteristics similar to the first, electrically insulating material, but which exhibits electrical conductivity higher than the electrical conductivity of the first, electrically insulating material. In some exemplary embodiments, the second, electrically conductive material is silicone rubber with the addition of one or more materials that increase the electrical conductivity of the material. Normally, additives that increase the electrical conductivity of the silicone rubber material can adversely affect the mechanical properties of the silicone rubber. For example, added conductive materials can cause the silicone rubber to exhibit higher hardness (e.g., less flexibility) than the silicone rubber without the added materials. It is desired to substantially maintain the overall flexibility of the surgical port feature 238, including the first and second electrically conductive portions 258, 260. Accordingly, the disclosure provides embodiments of surgical port features that include electrically conductive portions made from materials that exhibit a relatively high level of flexibility compared to other conductive materials.

For example, in exemplary embodiments of the disclosure, the first and second electrically conductive portions 258, 260 are made from a composite material having a continuous phase of silicone rubber material and a discontinuous phase of carbon particulates dispersed throughout the continuous phase. In exemplary embodiments, the carbon particulates are in the form of fibers and are added to the pre-molded silicone rubber raw materials and molded with the silicone rubber to form the first and second electrically conductive portions 258, 260. As additional non-limiting examples, the fibers can optionally include nickel-plated carbon fibers, nano-scale carbon materials such as carbon nanotubes, and other similar materials.

In some exemplary embodiments, carbon fiber rods prior to mixing have a length of several millimeters (mm), such as ranging from 1 mm to 20 mm, and a diameter of several micrometers (μm), such as ranging from 5 μm to 15 μm. In one exemplary embodiment, the carbon fiber rods have a length of 12-13 mm prior to mixing and a diameter of 10 μm. As further non-limiting examples, the carbon fiber rods before mixing with the silicone rubber raw materials exhibit a length to diameter ratio of greater than 5:1, greater than 10:1, greater than 20:1, greater than 50:1, greater than 100:1, etc.

As a non-limiting example, the carbon fiber rods exhibit a tensile strength of greater than 1000 MPa (145,000 psi). As a more specific non-limiting example, the carbon fiber rods exhibit a tensile strength of 1207 MPa (175000 psi). In some embodiments, the tensile strength may exceed 3000 MPa, 4000 MPa, or more. According to an exemplary embodiment, the carbon fiber rods exhibit a tensile modulus (i.e., elastic modulus under tensile stress conditions) of greater than 100 GPa (14,500 kpsi). For example, in an exemplary embodiment, the carbon fiber rods exhibit a tensile modulus of 137 GPa (20,000 kpsi). In some embodiments, the tensile modulus may exceed 175 GPa, 200 GPa, or more.

According to various exemplary embodiments, the carbon fiber rods are mixed with the silicone rubber raw materials at a volume percent ranging from 1 volume percent (vol %) to 10 vol %, for example from 4 vol % to 5 vol %. In some exemplary embodiments, the carbon fiber rods are mixed with the silicone rubber raw materials at a weight percent ranging from 0.1 weight percent (wt %) to 5 wt %, for example the weight percent can be 1.5 wt %.

The weight or volume percent of carbon fiber added to the silicone rubber is dependent at least partly on the tensile modulus of the carbon fibers. Stronger carbon fibers (e.g., those with a higher tensile modulus) are less likely to break during mixing with the silicone rubber raw materials, resulting in longer lengths of carbon fiber rods in the final molded component. This can result in more ready formation of electrically conductive networks with one another and result in enhanced overall electrical conductivity of the final component for a given weight or volume percent of the carbon fiber rods. Conversely, weaker carbon fiber rods break into smaller lengths during mixing and do not form conductive networks with one another as readily due to their shorter length, and thereby can result in relatively lower electrical conductivity for a given weight or volume percent, as compared to a stronger carbon fiber. Sufficient tensile modulus, such as the ranges of tensile modulus values noted above, and sufficient starting length of the carbon fiber rods can help to ensure that the carbon fiber rods maintain, on average, a length of greater than 1 mm, or greater than 3 mm, greater than 5 mm, etc. In exemplary embodiments, the carbon fiber rods exhibit an average post-mixing length ranging from 6 mm to 12 mm.

Carbon fibers suitable for use in disclosed exemplary embodiments are available from suppliers such as, for example, Toho Tenax America, Inc., Rockwood, Tenn., USA; Cytec Industries Inc., Woodland Park N.J., USA; and Asbury Carbons, Asbury, N.J., USA. Some carbon fibers are supplied with sizing treatments (i.e., a chemical coating over the fiber that improves bonding of the fiber with the resins or other polymers typically used in carbon fiber composite materials) that may potentially interfere with (e.g., reduce) the electrical conductivity between the carbon fiber rods once the carbon fiber rods are incorporated into the silicone rubber material. Accordingly, in some exemplary embodiments, any sizing present on the carbon fiber rods is removed from the rods prior to mixing with the silicone rubber material to promote electrical conductivity between the carbon fiber rods. For example, the carbon fiber rod particles are immersed in a solvent under low pressure conditions (e.g., within a vacuum chamber) to remove the sizing.

In exemplary embodiments, the surgical port feature 238 is formed using injection molding in a two-step process. The body portion 256 of the surgical port feature 238 is first injection molded from a material having strength, elasticity, and other material characteristics as discussed above, such as, for example, silicone rubber. The body portion 256 includes negative portions (i.e., areas devoid of material) where the first and second conductive portions 258, 260 are to be located. Following molding of the body portion 256, the first and second conductive portions 258, 260 are overmolded in the negative portions of the body portion 256 with electrically conductive material, such as silicone rubber with the addition of carbon fiber rods, as discussed above. While injection molding is specifically mentioned, any other suitable manufacturing processes are considered as within the scope of the disclosure. For example, surgical ports according to exemplary embodiments of the disclosure optionally are manufactured by casting, additive and/or subtractive processes, other processes, and combinations thereof.

As shown in FIG. 2, the first and second electrically conductive portions 258, 260 extend between an interior surface of one or more of the channels 246, 248, 250 and an outer surface of the surgical port feature 238 proximate the waist portion 244 of the surgical port feature 238. The first and second electrically conductive portions 258, 258 made from the electrically conductive material are located and configured to form an electrically conductive path between a cannula of a surgical instrument (e.g., any one of cannulas 235, 236, and 237 in FIG. 3) and the body wall of the patient. For example, contact between the cannula and the electrically conductive portion 258, 260 within one of the channels 246, 248, 250 forms a path for dissipation of electrical current from a surgical instrument positioned within the cannula to the patient body potential (e.g., reference potential, ground, etc.). In some exemplary embodiments, the electrically conductive portions are configured to form separate electrically conductive paths for one or more of the instruments associated with each cannula (e.g., each of cannula 235, 236, and 237 in FIG. 3), as discussed below.

Figure 4:
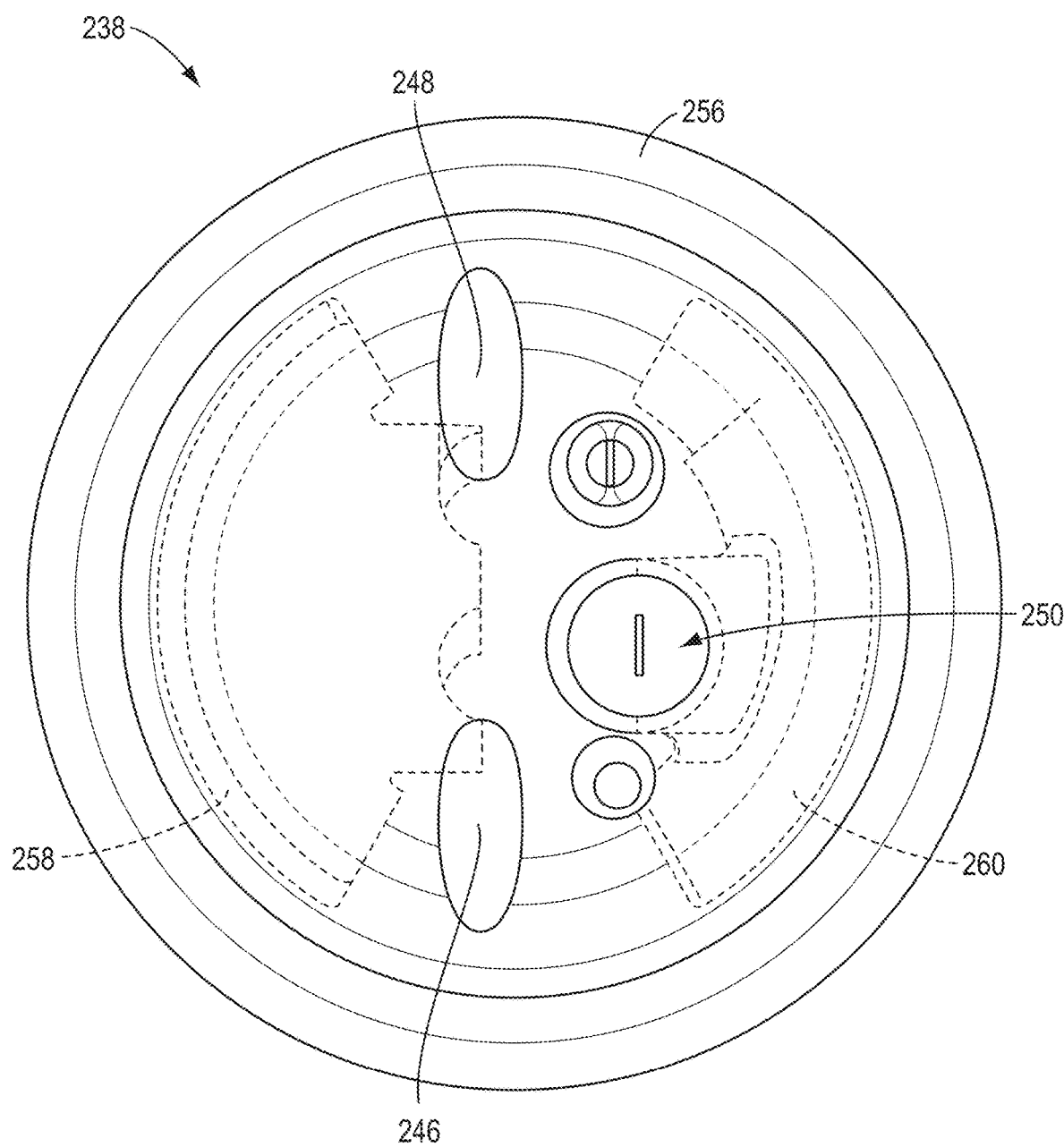
FIG. 4 is an interior plan view of the surgical port according to the exemplary embodiment of FIG. 2.

For example, referring now to FIG. 4, a plan view of the surgical port feature 238 according to the exemplary embodiment of FIG. 2 is shown. The surgical port feature 238 includes an electrically insulative body portion 256 and two electrically conductive portions 258, 260 shown by hidden lines. The two electrically conductive portions 258, 260 intersect channels 246, 248, 250 formed between the upper flange 240 and the lower flange 242 of the surgical port feature 238, through which passages the cannulas 235, 236, and 237 may respectively be positioned (as shown in FIG. 3).

In some embodiments, due to differing electrical operational characteristics between the surgical instruments and the endoscope, it is desirable to electrically isolate the endoscope (e.g., an endoscope positioned within the endoscope cannula 237 shown in FIG. 3) from the instruments (e.g., instruments positioned within instrument cannulas 235, 236 shown in FIG. 3). As shown in FIG. 4, the first electrically conductive portion 258 intersects channels 246 and 248, and the second electrically conductive portion 260 intersects channel 250. In the embodiment of FIG. 4, the channels 246 and 248 are configured to accept cannulas 235, 236 associated with surgical instruments, while the channel 250 is configured to accept cannula 237 associated with an imaging device such as an endoscope. The first electrically conductive portion 258 is separated from the second electrically conductive portion 260 by portions of the electrically insulating material of the body portion 256, thereby electrically insulating the first and second electrically conductive portions 258 and 260 from one another.

Figure 5:
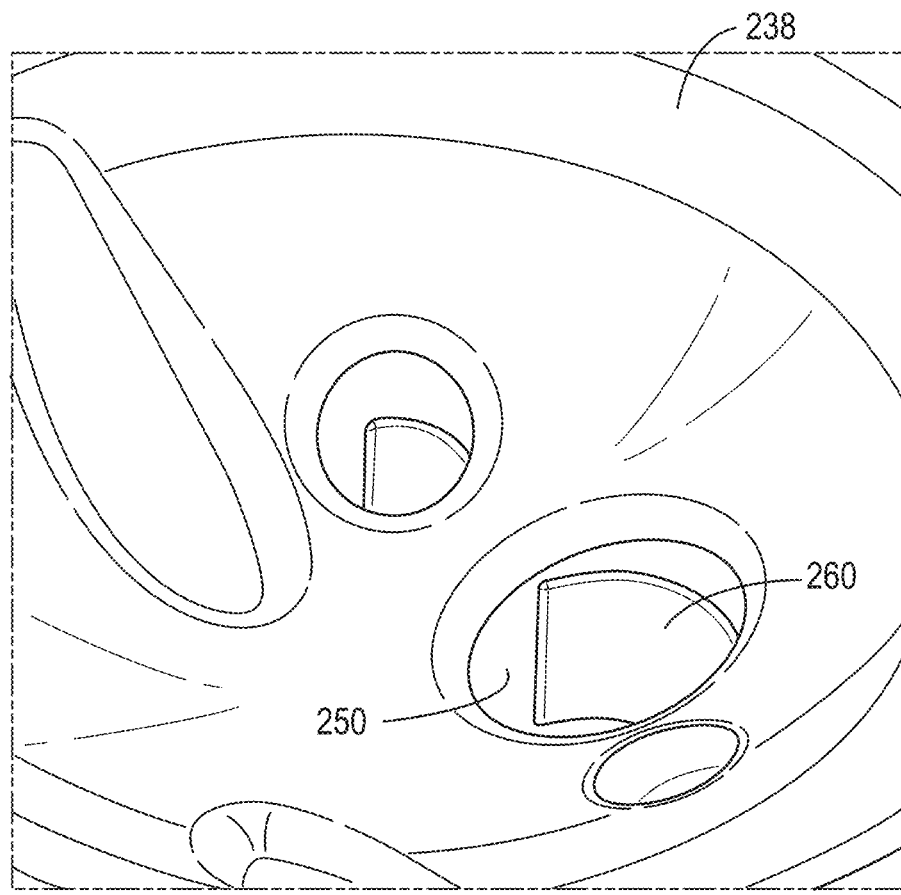
FIG. 5 is a detailed perspective view of the surgical port according to the exemplary embodiment of FIG. 2.

In order to ensure consistent and secure contact between the cannulas 235, 236, and 237 (FIG. 3) with the respective electrically conductive portions 258, 260, the electrically conductive portions 258, 260 optionally extend partly into one or more of the channels 246, 248, and 250 beyond a surface of the channel(s) that is defined by the body portion 256. In other words, the electrically conductive portions 258, 260 are configured to form an interference fit within the channels 246, 248, 250 with a respective one of the cannulas 235, 236, and 237. For example, referring to FIG. 5, channel 250 is shown in a perspective, enlarged view of the port 238. A portion of the second electrically conductive portion 260 extends into the channel 250 beyond a surface of the channel defined by the body portion 256 to provide secure contact with the cannula 237 (FIG. 3) and ensure electrical conductivity between the cannula 237 and the second conductive portion 260. Similarly, the first electrically conductive portion 258 (not shown in FIG. 5) may extend into the channels 246, 248 (FIG. 4) to ensure secure contact and electrical conductivity between the cannulas 235, 236 (FIG. 3) and the first electrically conductive portion 258.

In exemplary embodiments, the first and second electrically conductive portions 258, 260 extend into the channels 246, 248 and 250 by 1 millimeter (0.04 inches) or less past the surface of the channels formed by the body portion 256. As a non-limiting example, the first and second electrically conductive portions 258, 260 extend into the channels 246, 248 and 250 by 0.5 millimeters (0.02 inches) or less. As a further non-limiting example, the first and second electrically conductive portions 258, 260 extend into the channels 246, 248, and 250 by 0.254 mm (0.010 inches). As another non-limiting example, the first and second electrically conductive portions 258, 260 extend into the channels 246, 248, and 250 by 0.1 millimeter (0.004 inches) to 1.0 millimeter (0.04 inches). However, other configurations are contemplated, such as one or both of the first and second electrically conductive portions 258, 260 extending into the channels 246, 248, 250 by less than 0.254 millimeters or by greater than 1 millimeter.

Figure 6:
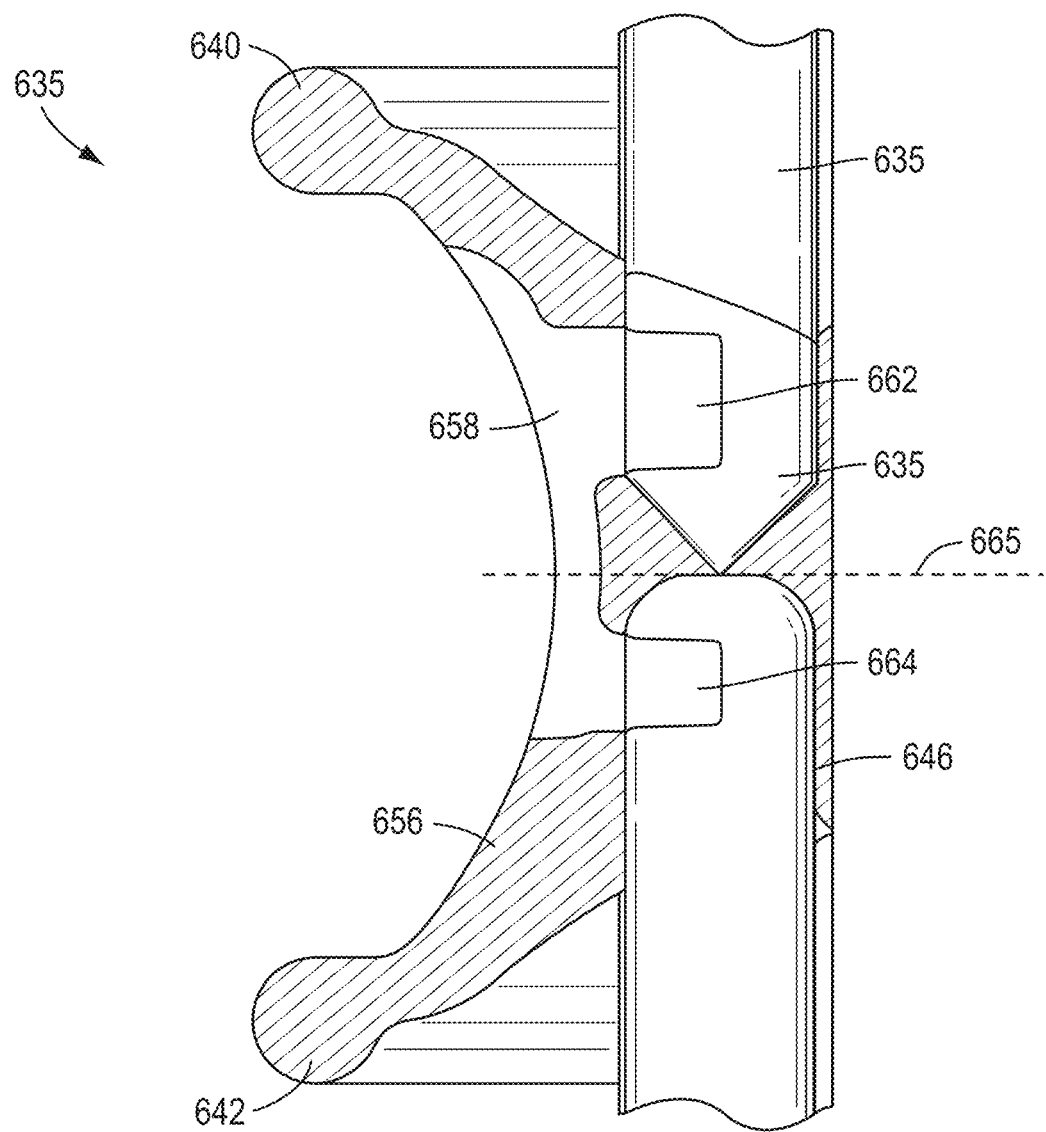
FIG. 6 is a cross-sectional partial elevation view of a surgical port according to another exemplary embodiment of the disclosure.

In some exemplary embodiments, the location and shape of the electrically conductive portions is asymmetrical between the upper flange and lower flange of the surgical port. For example, as shown in FIG. 6, a surgical port feature 638 includes a body portion 656 made from an electrically insulating material, and an electrically conductive portion 658 made from an electrically conductive material, such as the electrically conductive material described above. The electrically conductive portion 658 includes first and second protrusions 662 and 664 that extend into channel 646 to contact the cannula 635 above and below a center of motion of the cannula 635 positioned along line 665. In an exemplary embodiment, the line 665 falls on a midplane of the surgical port feature 638 between the upper flange 640 and the lower flange 642. Providing points of contact above and below the center of motion of the cannula 635 can help to ensure that the electrically conductive portion 658 remains in contact with the cannula 635 during articulation of the cannula 635 about the center of motion.

While the use of carbon fiber rods for imparting electrical conductivity to the electrically conductive portion 658 as described above results, in some embodiments, in the electrically conductive portion 658 having flexibility similar to the flexibility of the body portion 256, other mechanical characteristics of the material may be altered from the material of the body portion 656. For example, in some exemplary embodiments, presence of the carbon fiber rods potentially affects the tensile strength of the continuous phase material (e.g., silicone rubber) of the electrically conductive portion 658. Additionally, excessive manipulation (e.g., deformation) of the electrically conductive portion 656 could potentially cause the electrically conductive portion to tear or otherwise separate from the body portion 656 under certain conditions, or could lead to tearing within the electrically conductive portion 656.

Accordingly, in the embodiment of FIG. 6, the electrically conductive portion 658 is located between an upper flange 640 and lower flange 642 of the surgical port feature 238. Because the amount of movement of the cannula 635 for a given articulation increases with distance from the center of motion, the electrically conductive portion 658 is optionally located proximate the center of motion (e.g., the line 665) to minimize deformation of the electrically conductive portion 658 resulting from articulation of the cannula 635.

Additionally, in some exemplary embodiments, the electrically conductive portion 658 is optionally offset in an axial direction (e.g., a direction extending between the upper flange 640 and lower flange 642) toward the upper flange 640 of the surgical port feature 638 to reduce deformation to the electrically conductive portion 658 during insertion of the surgical port feature 638 into an incision in the patient's body. For example, during some surgical procedures, a surgeon or other operating room staff may use a clamp to laterally flatten the lower flange 642 for insertion of the lower flange 642 in an incision in the patient's body wall (e.g., body wall 204 shown in FIG. 3). The offset of the electrically conductive portion 658 in an axial direction toward the upper flange 640 as shown in the embodiment of FIG. 6 reduces the deformation occurring in the electrically conductive portion 658 and thereby potentially reduces the likelihood of damage to the electrically conductive portion 658 during insertion of the lower flange 642 of the surgical port feature 638.

Figure 7:
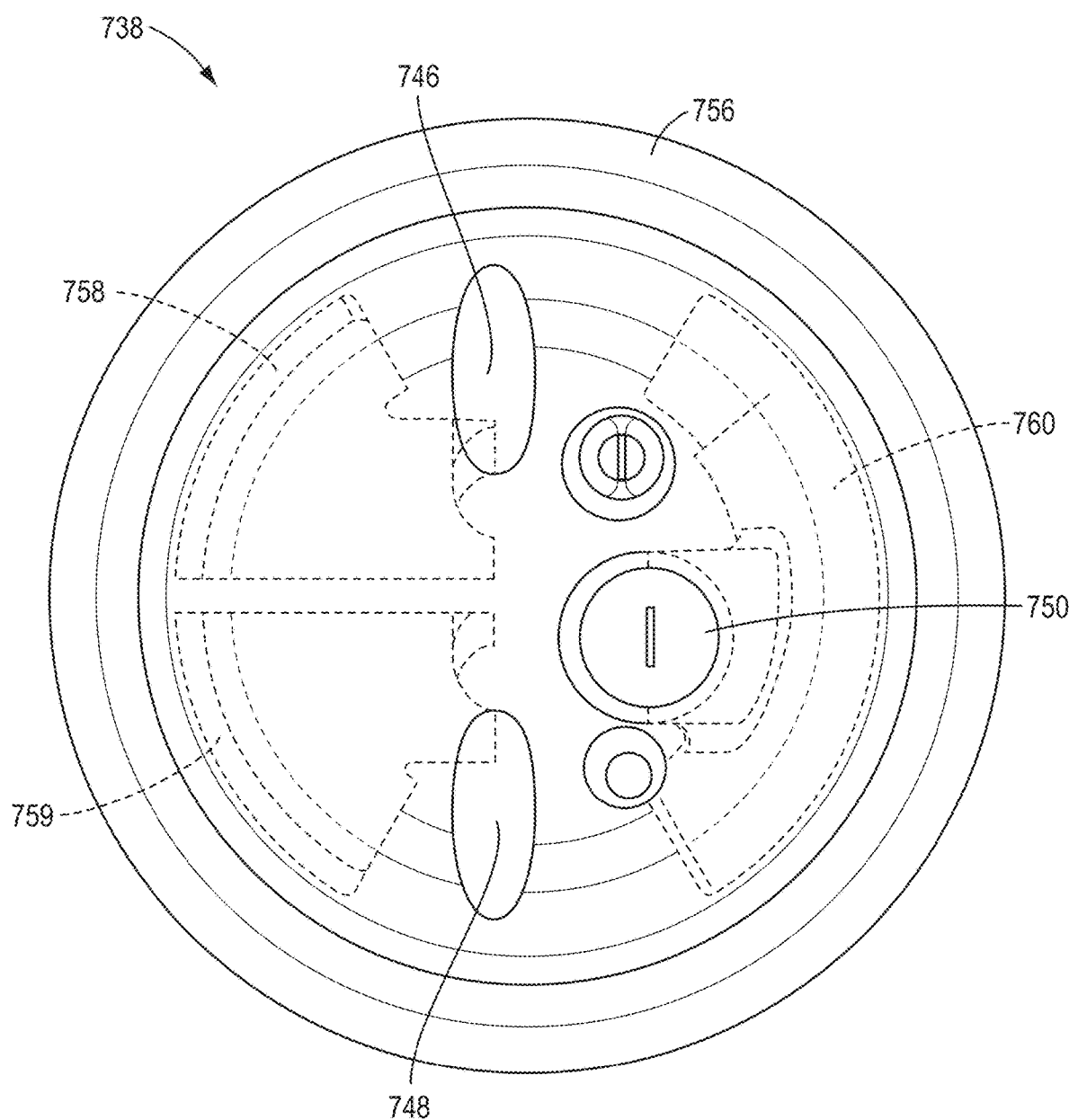
FIG. 7 is an interior plan view of a surgical port according to another exemplary embodiment of the disclosure.

Referring now to FIG. 7, another exemplary embodiment of a surgical port feature 738 is shown. In the embodiment of FIG. 7, the surgical port feature 738 includes a body portion 756 made from an electrically insulating material. The surgical port feature 738 further includes a first electrically conductive portion 758, a second electrically conductive portion 759, and a third electrically conductive portion 760, all shown by hidden lines. Each of the electrically conductive portions 758, 759, and 760 are electrically isolated from one another by the electrically insulating material of the body portion 756. Each of electrically conductive portions 758, 759, and 760 intersects a respective one of the channels 746, 748, and 750. Thus, cannulas inserted into each of the channels 746, 748, and 750, and instruments within each cannula, are electrically isolated from one another by the material of the body portion 756 of the port 738 and individually and separately grounded to the patient's body by a respective one of the electrically conductive portions 758, 759, and 760.

Figure 8:
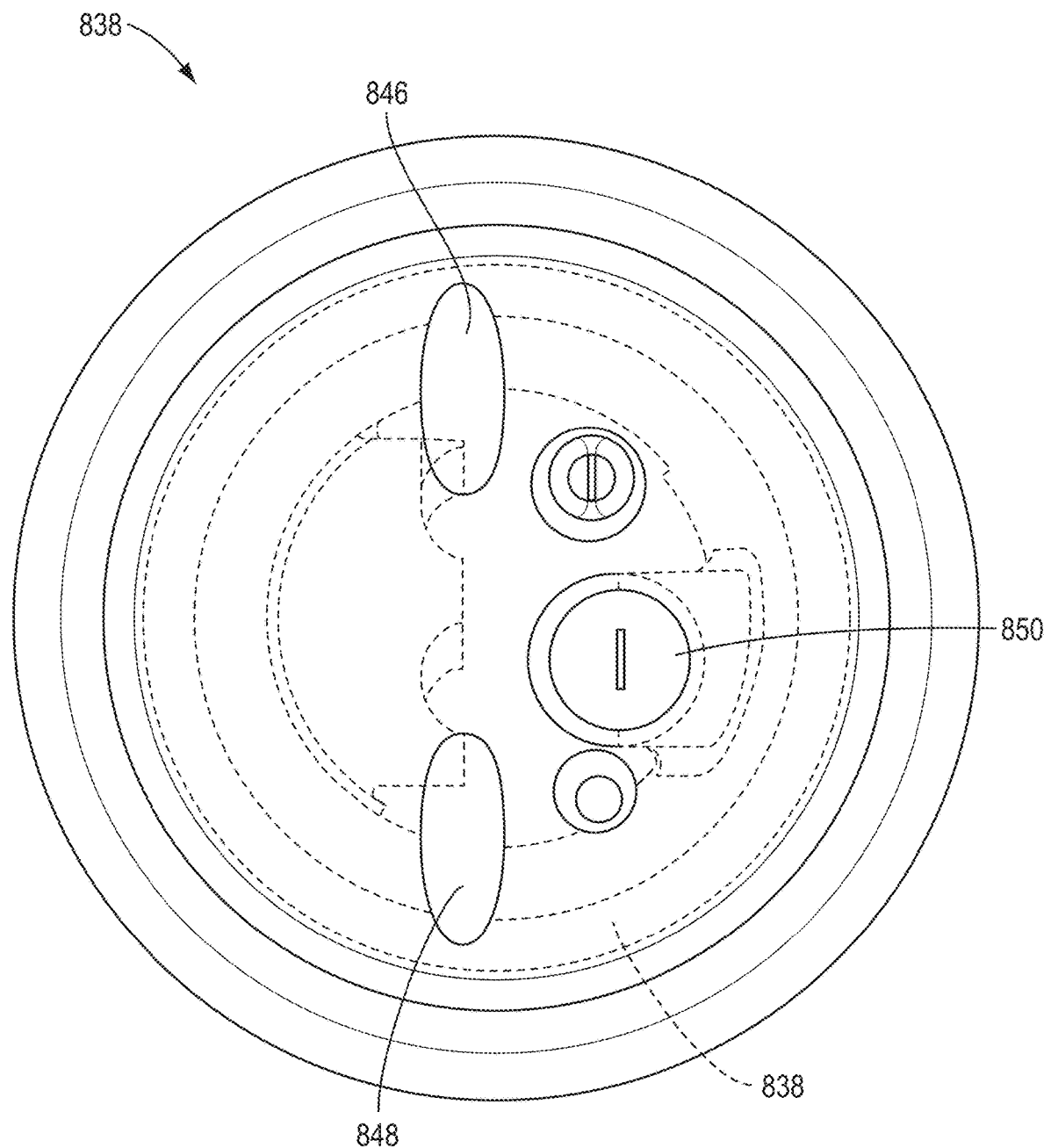
FIG. 8 is an interior plan view of a surgical port according to yet another exemplary embodiment of the disclosure.

In some exemplary embodiments, there is no need to isolate the various instruments from one another as in the exemplary embodiment of FIG. 7. Thus, in yet other exemplary embodiments, all the channels of a surgical port may be intersected by a single electrically conductive portion, thereby grounding all instruments to body ground together. For example, referring now to FIG. 8, an exemplary embodiment of a surgical port feature 838 includes a conductive portion 858 (shown by hidden lines) that intersects all three channels 846, 848, and 850. The conductive portion 858 creates a common ground path between the channels (and any cannulas or instruments inserted therein) and the body of the patient. Such an embodiment can be used in situations where there is no need to isolate the various instruments from one another. For example, when the various instruments have similar electrical operational characteristics, grounding the various instruments through a common ground path potentially does not lead to capacitive coupling between the instruments, and the surgical port feature 838 with the single conductive portion 858 could be used in such a situation.

Various exemplary embodiments of the present disclosure provide surgical port features having the capability of dissipating electrical energy to a reference electrical potential (e.g., body ground, "zero" voltage, etc.) while maintaining flexibility to facilitate insertion of the surgical port feature within the patient's body and facilitate articulation of cannulas placed within channels of the port feature, while maintaining good electrical contact with the cannulas.

This description and the accompanying drawings that illustrate exemplary embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

Further modifications and alternative embodiments will be apparent to those of ordinary skill in the art in view of the disclosure herein. For example, the devices and methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with the following claims being entitled to their fullest breadth, including equivalents, under the applicable law.

What is claimed is:

1. A surgical port, comprising:
   an electrically insulating body portion comprising:
      a first end,
      a second end opposite the first end, and
      a sidewall defined between the first end and the second end;
   a channel extending through the electrically insulating body portion from the first end to the second end, the channel comprising an inner surface surrounding an interior volume sized to receive a cannula; and
   an electrically conductive material portion extending from the channel through the body portion to the sidewall, the electrically conductive material portion extending into the interior volume of the channel beyond the inner surface of the channel,
   wherein the electrically conductive material portion does not entirely surround the channel in a transverse cross-section at a position along a length of the channel at which the electrically conductive material extends into the interior volume.

2. The surgical port of claim 1, wherein a distance the first electrically conductive material portion extends beyond the inner surface of the first channel ranges from 0.1 mm to 1.0 mm.

3. The surgical port of claim 1, wherein the electrically conductive material portion comprises:
   a first protrusion extending into the interior volume of the channel at a first location; and
   a second protrusion extending into the interior volume of the channel at a second location;
   the first protrusion and the second protrusion being separated at the inner surface of the channel by a portion of the electrically insulating body portion.

4. The surgical port of claim 1, wherein:
   the channel is a first channel;
   the electrically conductive material portion is a first electrically conductive material portion;
   the surgical port comprises a second channel extending through the electrically insulating body portion from the first end to the second end, the second channel comprising an inner surface surrounding an interior volume sized to receive a cannula; and
   the surgical port comprises a second electrically conductive material portion, the second electrically conductive material portion extending into the interior volume defined by the inner surface of the second channel.

5. The surgical port of claim 4, wherein the first electrically conductive material portion and the second electrically conductive material portion are electrically insulated from one another by the electrically insulating body portion.

6. The surgical port of claim 1, wherein the electrically conductive material portion comprises a composite material.

7. The surgical port of claim 6, wherein:
the composite material comprises a continuous phase and a discontinuous phase;
the continuous phase comprises a polymer matrix; and
the discontinuous phase comprises electrically conductive particles.

8. The surgical port of claim 7, wherein the electrically conductive particles are rod shaped.

9. The surgical port of claim 7, wherein the electrically conductive particles comprise carbon fiber.

10. The surgical port of claim 7, wherein the polymer matrix comprises a silicone rubber.

11. The surgical port of claim 1, wherein:
a longitudinal axis of the surgical port is defined between the first end and the second end;
the longitudinal axis defines a longitudinal direction; and
the electrically conductive material portion is offset between the first end and the second end along the longitudinal direction.

12. A surgical port, comprising:
an electrically insulating body portion, a channel extending through the electrically insulating body portion, and an electrically conductive material portion;
wherein the electrically insulating body portion comprises a first end, a second end opposite the first end, a longitudinal axis extending through the first end and the second end, and a sidewall surrounding the longitudinal axis between the first end and the second end;
wherein the channel has a length extending from the first end to the second end;
wherein the channel comprises an inner surface surrounding an interior volume sized to receive a cannula;
wherein the electrically conductive material portion extends from the interior volume of the channel through the body portion to the sidewall;
wherein the electrically conductive material portion intersects the inner surface of the channel at two separate locations spaced apart along a length of the channel; and
wherein the electrically conductive material portion does not entirely surround the channel in a transverse cross-section at the two separate locations.

13. The surgical port of claim 12, wherein:
a midplane of the electrically insulating body portion is defined normal to the longitudinal axis and half-way between the first end and the second end; and
the two separate locations are on opposite sides of the midplane of the electrically insulating body portion.

14. The surgical port of claim 12, wherein:
the longitudinal axis defines a longitudinal direction;
a remote center of motion is defined for a cannula received in the channel; and
the two separate locations are on opposite sides of the remote center of motion along the longitudinal direction.

15. The surgical port of claim 12, wherein the electrically conductive material portion extends into the interior volume of the channel beyond the inner surface of the channel.

16. The surgical port of claim 15, wherein a distance the electrically conductive material portion extends beyond the inner surface of the channel ranges from 0.1 mm to 1.0 mm.

17. The surgical port of claim 12, wherein:
the electrically conductive material portion comprises a composite material;
the composite material comprises a continuous phase and a discontinuous phase;
the continuous phase comprises a polymer matrix; and
the discontinuous phase comprises electrically conductive particles.

18. The surgical port of claim 17, wherein the polymer matrix comprises silicone rubber.

19. The surgical port of claim 17, wherein the electrically conductive particles comprise carbon fiber.

* * * * *

UNITED STATES PATENT AND TRADEMARK OFFICE
CERTIFICATE OF CORRECTION

| | | |
|---|---|---|
| PATENT NO. | : 11,707,613 B2 | Page 1 of 1 |
| APPLICATION NO. | : 16/825421 | |
| DATED | : July 25, 2023 | |
| INVENTOR(S) | : Michael Hurst, Sam Crews and Bryan E. Blair | |

It is certified that error appears in the above-identified patent and that said Letters Patent is hereby corrected as shown below:

In the Claims

Column 12, Claim 2, Line 44, delete "first".

Signed and Sealed this
Twenty-sixth Day of December, 2023

Katherine Kelly Vidal
*Director of the United States Patent and Trademark Office*